(12) United States Patent
Moore et al.

(10) Patent No.: US 10,453,567 B2
(45) Date of Patent: Oct. 22, 2019

(54) SYSTEM, METHODS, AND DEVICES FOR IMPROVING SLEEP HABITS

(71) Applicant: Sleep Orbit Inc., Spokane, WA (US)

(72) Inventors: Jason Moore, Spokane, WA (US); Chris Mirabzadeh, Pullman, WA (US)

(73) Assignee: Sleep Orbit Inc., Spokane, WA (US)

( * ) Notice: Subject to any disclaimer, the term of this patent is extended or adjusted under 35 U.S.C. 154(b) by 239 days.

(21) Appl. No.: 15/497,023

(22) Filed: Apr. 25, 2017

(65) Prior Publication Data

US 2018/0303412 A1  Oct. 25, 2018

Related U.S. Application Data

(60) Provisional application No. 62/327,926, filed on Apr. 26, 2016.

(51) Int. Cl.
| | |
|---|---|
| *A61B 5/00* | (2006.01) |
| *A61M 21/02* | (2006.01) |
| *G06F 19/00* | (2018.01) |
| *G16H 20/30* | (2018.01) |
| *G16H 80/00* | (2018.01) |
| *G16H 50/20* | (2018.01) |
| *G16H 20/70* | (2018.01) |

(52) U.S. Cl.
CPC ............ *G16H 20/30* (2018.01); *G16H 20/70* (2018.01); *G16H 50/20* (2018.01); *G16H 80/00* (2018.01)

(58) Field of Classification Search
CPC ........ G16H 20/30; G16H 80/00; G16H 20/00; A61B 5/4812; A61B 5/4815; A61B 5/0022; A61B 5/486; A61B 5/4809
See application file for complete search history.

(56) References Cited

U.S. PATENT DOCUMENTS

| | | | | |
|---|---|---|---|---|
| 2006/0287883 A1* | 12/2006 | Turgiss | ............... | G06F 19/3418 705/2 |
| 2011/0015495 A1* | 1/2011 | Dothie | ................... | G16H 10/60 600/300 |

* cited by examiner

*Primary Examiner* — Christine H Matthews
*Assistant Examiner* — Joshua Daryl D Lannu
(74) *Attorney, Agent, or Firm* — Lee & Hayes, P.C.

(57) ABSTRACT

Systems, methods, and devices that provide personalized sleep improvement programs for improving sleep habits are described. The personalized sleep improvement programs may include sleep characteristics of a user, at least one factor impacting a sleep of the user, at least one sleep goal for the user, and a sleep-related performance of the user.

10 Claims, 14 Drawing Sheets

900 ⟶

906 ⟶

Section 1 Exterior Environment

904 ⟶ Do any of the following noises from outside your home disturb your sleep or wake you up?

☑ Loud neighbors

904 ⟶ How often?
- ○ Once a month or less than once a week
- ○ 2 or 3 days a week
- ○ 2 or 3 days a week
- ○ 2 or 3 days a week 904 ⟶ How many times does it happen during that sleep time?
- ○ 1
- ○ 2

Finish Later    Continue

SYSTEM, METHODS, AND DEVICES FOR IMPROVING SLEEP HABITS

RELATED APPLICATION

This application claims the benefit of priority to provisional U.S. Patent Application Ser. No. 62/327,926, filed on Apr. 26, 2016 and entitled "System, methods, and devices for improving sleep habits", which is herein incorporated by reference in its entirety.

BACKGROUND

An important consideration in a person's health is sleep. The consensus in the medical field today considers sleep, diet, and exercise to function as three pillars crucial to a person's health. Lack of sleep may contribute to an increase in illness such as heart disease, stroke, cancer, chronic respiratory diseases, obesity and diabetes. Moreover, lack of sleep may also increase accidents. For example, a lack of sleep may cause an increase in accidents on and off of a job.

Professional help exists that may improve a person's sleep. For example, professional help exists that may focus mainly on treating medically diagnosable sleep disorders. However, there are limited options for people without serious sleep disorders, such as sleep apnea, restless leg, chronic insomnia, or with a diagnosed mental illness, to receive help to improve their sleep habits. For example, for people without medically diagnosed or diagnosable sleep conditions, finding quality sleep advice becomes difficult as they must rely on basic information from a General Practitioner. In another example, people must rely on self-directed treatment methods.

Moreover, in many instances options for people seeking sleep assistance may be limited to: expensive medical programs which often treat sleep conditions with medical devices and/or prescription medicines; professional advice from mental health providers who may offer limited supervision and/or advice on how to modify sleep behaviors; advice from general practitioners who may provide the person with standardized information about the need for better sleep and/or offer prescription sleep aids; self-help methods such as over-the-counter medicines; non-certified sleep improvement applications on mobile devices; and advice websites that make suggestions for improving sleep.

While websites and mobile applications may provide people with options that can help improve sleep quality, they are self-directed support options and do not offer personal, professional assistance. To achieve guided support when modifying sleep behaviors, consumers must rely on medical help through sleep clinics or with the assistance of a sleep doctor. There are currently no consumer-level sleep counseling programs for the general public to engage in preventative sleep modification.

Additionally, within the sleep improvement industry there are proven tools to improve sleep health. For example, people with sleep apnea may be provided with continuous positive airway pressure (CPAP) machines that assist them with breathing. As another example, people who suffer from insomnia may be provided with sleep medications. Further, people who have mental illness may receive coaching from a mental health care professional as part of a treatment. However, people without these types of serious mental or physical health problems may find help improving their sleep with over the counter medications, by following information provided in advice columns, websites, etc., or they may find help by reducing stress through exercise.

In some instances, people may not improve their sleep for various reasons. For example, people with medically diagnosed sleep apnea may find the CPAP machine uncomfortable and choose not to use it. In another example, people taking medication may find that the medication does not adequately treat the condition and/or have unwanted side effects. In these examples, people who try to follow methods to improve their sleep behaviors without the aid of the CPAP machine or medication may not be successful. For example, people who try to follow methods to improve their sleep behaviors without the aid of CPAP machines or medication may find that they are unable to complete self-help improvement programs without guided support. Further, people may also find that information received from General Practitioners, websites, self-help sources, is inaccurate, out of date, impersonal, and/or does not provide the type of quality assistance they require.

Further, the cost associated with medical programs to improve sleep habits can be prohibitive. For example, people may choose to forego treatment programs, even when they are motivated to improve their sleep habits because the cost to participate in the medical programs can be too expensive and cost prohibitive. Moreover, in order to receive treatment at a sleep clinic or from a centerfield sleep professional people may have to have a qualifying condition prior to approval for treatment. In addition, people may encounter co-pays that are too expensive and cost prohibitive. For people without a qualifying condition, but who still wish to receive personal support to modify their sleep behaviors may also find that costs (e.g., out-of-the pocket costs) may be too expensive and cost prohibitive. Furthermore, sleep treatment may be difficult or impossible for people to find since the demand for sleep treatment may be high and/or space may not be available to provide them with a facility and/or service.

People who choose to make use of self-directed methods to improve their sleep may also face difficulties that lead to failure. For example, because people are using self-directed methods, they may not make the correct choices to provide them with the optimum treatment options to suit their needs. Their lack of expertise wastes their time and money on options that fail to correct their unhealthy sleep habits. People who fail to improve their sleep behavior may then endure unhealthy sleep habits that translate into higher incidents of illness and accidents and a decrease in productivity that negatively impacts the overall US economy.

Accordingly, there remains a need in the art for sleep programs found between the highly prescribed medical options and the unsupported self-help options, the sleep programs providing personalized counseling that follows well-researched and medically designed sleep behavioral improvement programs.

SUMMARY

Systems, methods, and devices for improving sleep habits are described which are configured to provide personalized counseling that follows well-researched and medically designed sleep behavioral improvement programs. Generally, the systems, methods, and devices fills a need for a personally designed sleep improvement program for people who may not have serious medical conditions, but still want to have guided assistance as they strive to improve their sleep. The systems, methods, and devices may utilize algorithms to determine more accurate measure of cumulative sleep/wake history by using additional data points to confirm or refute periods of activity beyond traditional less accurate methods of monitoring human rest/activity cycles. This summary is provided to introduce simplified concepts of systems, methods, and devices for improving sleep habits, which are further described below in the Detailed Description. This summary is not intended to identify essential features of the claimed subject matter, nor is it intended for use in determining the scope of the claimed subject matter.

In one example, a computerized method for providing sleep improvement for a user includes: receiving data identifying sleep characteristics of the user; associating the data identifying the sleep characteristics with an account of the user; assessing the associated data identifying the sleep characteristics; identifying at least one factor impacting a sleep of the user based at least in part on the assessing; generating a sleep improvement program for the user based at least in part on the identifying, the sleep improvement program including at least one goal for the user. In some examples, the computerized method may also include receiving data identifying at least one response by the user to at least one query, or data identifying at least one action taken by the user upon the user receiving the sleep improvement program. In some examples, the computerized method may also include determining a sleep-related performance of the user based at least in part on the data identifying the at least one response to the query by the user, or the data identifying the at least one action taken by the user.

In another example, a system including one or more processors and one or more non-transitory computer-readable media storing computer-executable instructions may perform actions that determine a sleep-related performance of a user. The actions may include receiving data identifying sleep characteristics of the user; assessing the data identifying the sleep characteristics; identifying at least one factor impacting a sleep of the user based at least in part on the assessing; receiving data identifying at least one response by the user to at least one query, or data identifying at least one action taken by the user; and determining a sleep-related performance of the user based at least in part on the data identifying the at least one response to the query by the user, or the data identifying the at least one action taken by the user.

In another example, a method for providing sleep improvement for a user may include providing, to a device associated with the user, a first Graphical User Interface (GUI) requesting data identifying sleep characteristics of the user. The method may also include providing, to the device associated with the user, a second GUI including at least one goal for the user based at least in part on data identifying the sleep characteristics of the user.

In another example, a method for providing sleep improvement for a user may include access data received by a device associated with the user to determine an environment of the user. For instance, the method may including accessing data from a cell phone, a thermostat, camera, microphone, gyroscope, accelerometer, or other dedicated sleep data device to determine a sleep characteristic of the user or an environment of the user. The method may also include providing, to the device associated with the user, a GUI including at least one goal or action for the user based at least in part on data received by the device associated with the user.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 9 illustrates a Graphical User Interface (GUI) for requesting data identifying sleep characteristics of a user.

DETAILED DESCRIPTION

Overview

Figure 1:
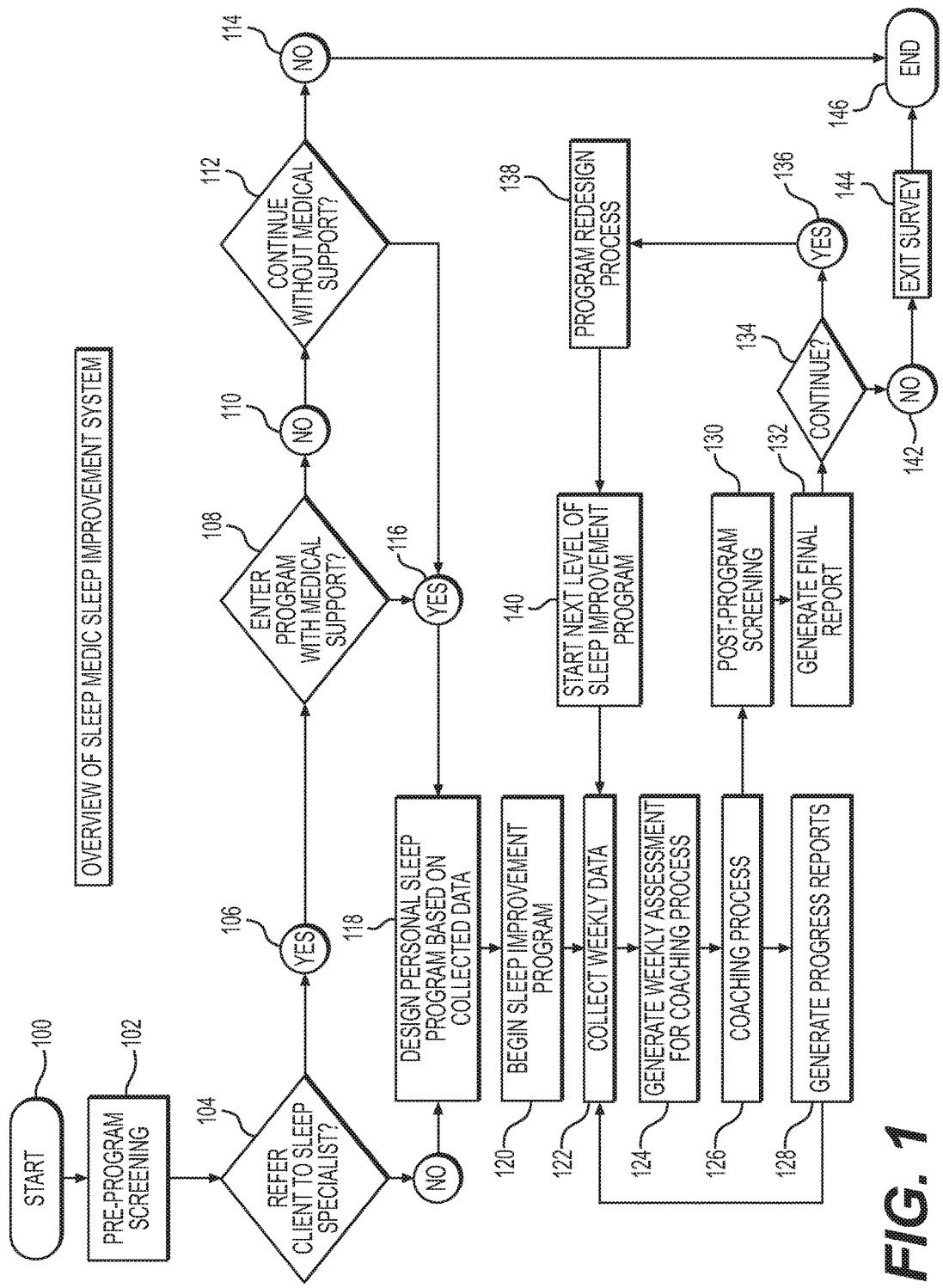
FIG. 1 illustrates a flow diagram of an example overview of a sleep improvement system.

This disclosure is directed to systems, methods, and devices that provide personalized sleep improvement programs for improving sleep habits. For example, systems, methods, and devices may provide personalized counseling that follows well-researched and medically designed sleep behavioral improvement programs, and fills a need for people who want to have guided and personalized assistance as they strive to improve their sleep. The methods may include computerized methods for providing a sleep improvement program to a user. The sleep improvement program may be generated by a computer based at least in part on identifying at least one factor impacting a sleep of the user. For example, the computer may assess data identifying sleep characteristics of the user, identify the at least one factor impacting the sleep of the user, and generate the sleep improvement program for the user. The sleep improvement program may include at least one goal for the user. The sleep improvement program provides personalized counseling to the user striving to improve his or her sleep because the sleep improvement program may be generated based on sleep characteristics of the user and factors impacting the sleep of the user.

In another example, systems may determine a sleep-related performance of a user. The sleep-related performance of the user may be determined by a computer based at least in part on data identifying at least one response to a query by the user, or the data identifying the at least one action taken by the user. For example, the computer may receiving data identifying sleep characteristics of the user, assess the data identifying the sleep characteristics of the user, identify at least one factor impacting a sleep of the user, receive data identifying at least one response by the user to at least one query, or data identifying at least one action taken by the user, and determining the sleep-related performance of the user based at least in part on the data identifying the at least one response to the query by the user, or the data identifying the at least one action taken by the user. The sleep-related related performance is personalized to the user striving to improve his or her sleep because the sleep-related related performance may be generated based on sleep characteristics of the user and/or current factors impacting the sleep of the user.

In another example, one or more Graphical User Interfaces (GUIs) may be provided to a device of a user to implement a sleep improvement program. For example, a first Graphical User Interface (GUI) requesting data identifying sleep characteristics of the user may be provided to the device of the user. The data identifying the sleep characteristics of the user may be received and/or assessed, and a second GUI may be provided to the device of the user that may include at least one goal for the user based at least in part on the data identifying the sleep characteristics of the user. Because the second GUI may include at least one goal for the user based at least in part on the data identifying the sleep characteristics of the user, the sleep improvement program is personalized to the user striving to improve his or her sleep.

In another example, a method may include accessing data from a cell phone, a thermostat, camera, microphone, gyroscope, accelerometer, or other dedicated sleep data device to determine a sleep characteristic of the user or an environment of the user. The data accessed from one or more of the devices may provide for generating a sleep improvement program for a user. For example, a system may access data from the cell phone, the thermostat, camera, microphone, gyroscope, accelerometer, or other dedicated sleep data device of a user to determine a sleep characteristic of the user or an environment of the user.

Illustrative Systems, Methods, and Devices for Improving Sleep Habits

FIG. 1 illustrates a flow diagram of an example overview of a sleep improvement system. Participants may start the program 100 by first participating in the pre-programming screening process 102. In some examples, participants may include people without serious sleep disorders, such as sleep apnea, restless leg, chronic insomnia, or with a diagnosed mental illness. In another example, participants may include people with serious sleep disorders, such as sleep apnea, restless leg, chronic insomnia, or with a diagnosed mental illness. The participant information may then be examined. Further, a trained professional may determine whether the participant needs to be referred to a professional sleep physician 104 for further evaluation of an existing or potential sleep disorder. Participants who receive a referral 106 may then be given the option to continue in the sleep program 108 while also receiving treatment for a diagnosed sleep disorder using an outside physician. Participants who choose not to seek medical treatment 110 for a possible sleep disorder may choose 112 to either not participate in the program 114 or participate in the sleep program 116 without additional medical support after signing a waiver. Participants who choose to participate in the program may then receive a personally designed sleep program 118. Participants who begin the sleep improvement program 120 may then begin providing data that is collected 122 to be analyzed. The data may be collected continuously during the program by one or more portable monitoring devices that may collect real-time vital data associated with a user. For example, portable monitoring device may be a bedside console, a mobile phone (e.g., smartphone), etc., that may collect and/or store data identifying information such as activity levels, pulse/heart rate, environmental noise, environmental temperature, body temperature, cortisol levels, etc. In some examples, the portable monitoring device may be communicatively coupleable to a wearable device (e.g., a wearable sleeve, an activity tracker, etc.). For example, a system may access data from a cell phone, a thermostat, a camera, a microphone, gyroscope, accelerometer, or other dedicated sleep data device of a user to determine a sleep characteristic of the user or an environment of the user.

The collected data may be analyzed 124 by a computer. The computer may receive data and use it to generate a coaching process 126. The computer may receive analyzed raw data and use it to generate progress reports 128. Participants repeat the collection, assessment, coaching process, and report generating process until they have completed the recommended sleep cycles. Participants may complete the post-program screening process 130. Participants may receive a final generated progress report 132 after their last day of participation and their post-screening process 130. Participants may have the option to continue 134 with another session of the sleep improvement program to further improve their sleep. Participants who choose to continue with the program 136 receive a redesigned sleep improvement program 138. Participants then start the next level 140. Participants who chose not to continue with the program 142 and complete the program may be given an exit survey 144 to help improve the quality of the sleep improvement program before they end 146 their participation in the program.

Figure 2:
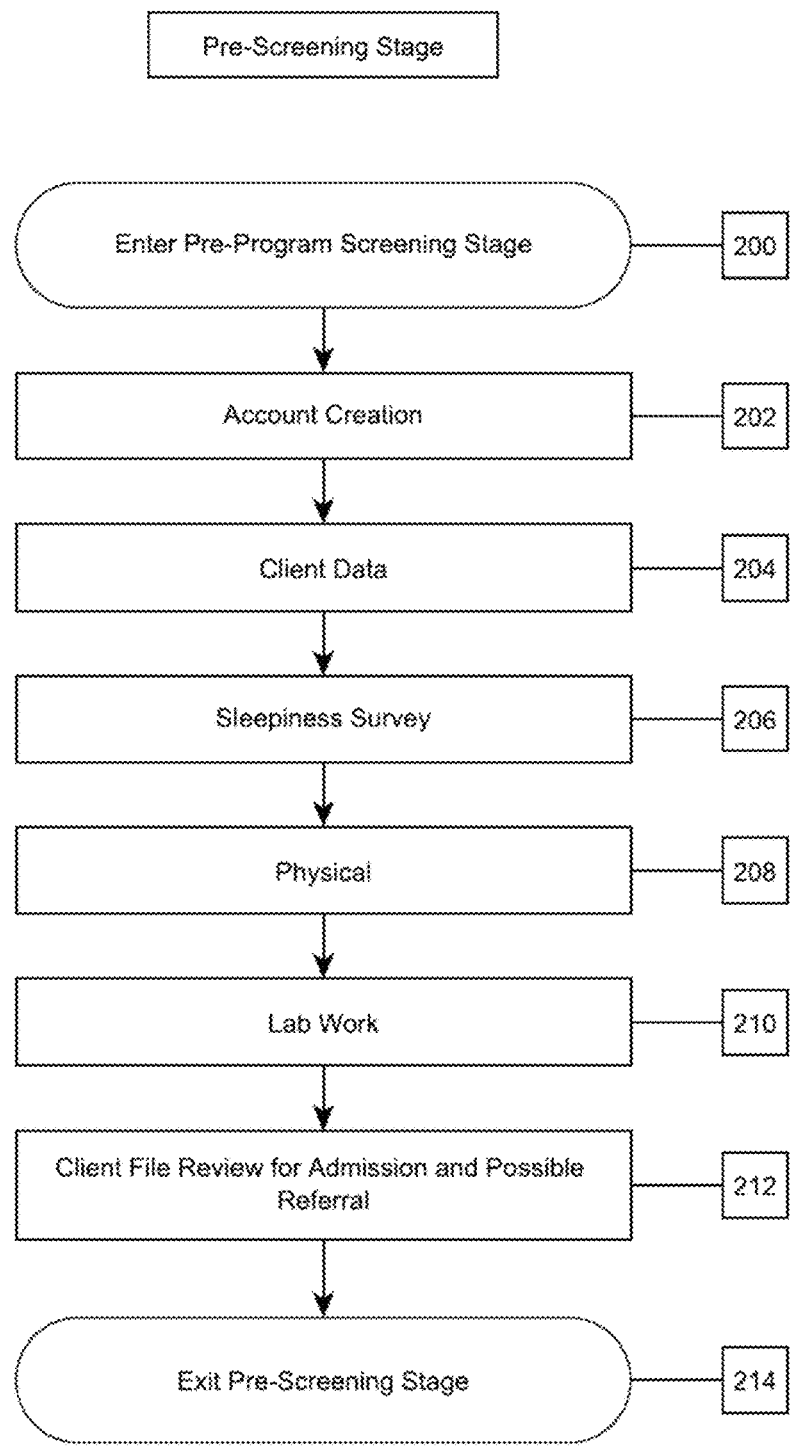
FIG. 2 illustrates a flow diagram of an example pre-screening process.

FIG. 2 illustrates a flow diagram of an example pre-screening process. Participants may enter the pre-screening stage 200. During the first step pre-screening stage, participants may create their program account 202. The program account may include a name of an associated user, a numeric password used to authenticate the associated user to the system, a transaction account or payment instrument of the associated user, an address of the associated user, identification of a device and/or application. During the second step of the pre-screening stage, participant data 204 may be collected. The participant data 204 may include medical history of the participant and details about the participant's sleep habits. The third step of the pre-screening stage may be a sleepiness survey 206. The participant may complete the sleepiness survey 206. The sleepiness survey may include a combination of validated questionnaires called "Sleepiness Scales." Sleepiness Scales may be "The Epworth Sleepiness Scale," "The national Sleep Foundation Sleepiness Test," "The Stanford Sleepiness Scale," or "The Karolinska Sleepiness Scale." The fourth step of the pre-screening stage may be a physical 208. The Participant may complete the physical 208 to provide further medical data regarding his or her beginning health status. The health status may include data representing a psychographic profile of the user, data representing a medical record of the user, the medical record including a record of a physical or a record of a lab value. In some examples, the data representing the health status of a participant may include the participant's body mass index (BMI), alcohol use, family history, etc. The participant may also receive a thorough blood laboratory work-up 210. After the data has been collected and/or received from the participant, the data may be examined to determine if the participant requires a referral 212 to a sleep professional for further evaluation for a possible sleep disorder. Participants may then exit 214 the pre-screening stage and continue to the next step of the sleep improvement program.

Figure 3:
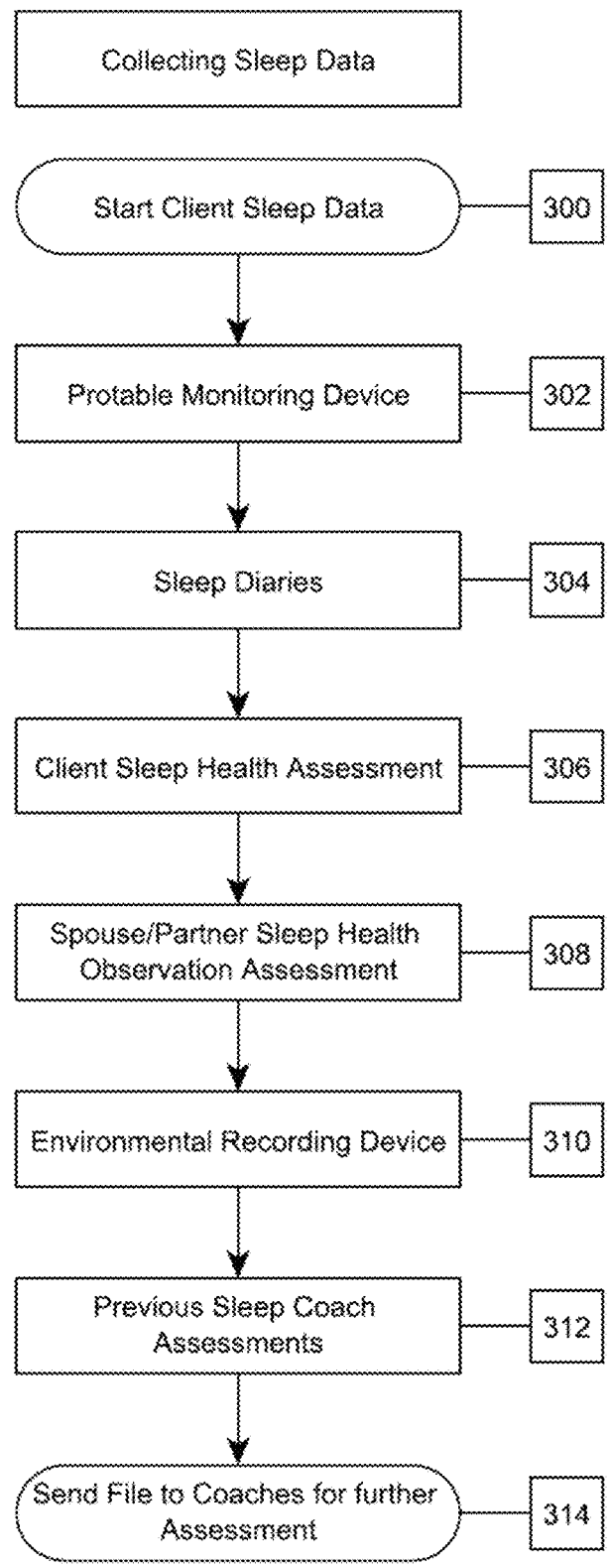
FIG. 3 illustrates a flow diagram of an example data collection process.

FIG. 3 illustrates a flow diagram of an example data collection process following the pre-screening stage of the sleep improvement program. The data collection process illustrated in FIG. 3 may represent participants beginning a sleep data collecting process 300. The sleep data collection process may include the participants receiving a portable monitoring device 302. The portable monitoring device may collect real-time vital data. For example, portable monitoring device may be a bedside console, a mobile phone (e.g., smartphone), etc., that may collect and/or store data identifying information such as activity levels, pulse/heart rate, environmental noise, environmental temperature, body temperature, cortisol levels, etc. In some examples, the portable monitoring device may be communicatively coupleable to a wearable device (e.g., a wearable sleeve, an activity tracker, etc.). In some examples, the portable monitoring device may include a heartbeat sensor. For example, the portable monitoring device may be a bedside console that includes a heartbeat sensor and/or a pulse oximeter that runs on 5 volts and an analog value processed to determine a user's heartbeat and/or oxygen saturation. The heartbeat sensor and/or pulse oximeter may be worn on a finger of a user.

Moreover, the portable monitoring device may be communicatively coupled to a control unit (e.g., environmental control unit (ECU)) for operating electronic devices, including heating, ventilation, air conditioning (HVAC) systems, appliances (e.g., refrigerator, microwave, oven, etc.), security systems, cameras, electric blinds, etc. In some examples, the portable monitoring device may be communicatively coupled to a control unit for operating the HVAC systems based on a user's sleep improvement program. For example, the portable monitoring device may determine that a user's sleep improvement program may include a goal to sleep in a cooler environment and determine that the HVAC system may be overheating the user's sleep environment. In this example, where the sleep improvement program includes a goal to sleep in cooler environment and the HVAC is overheating the user's sleeping environment, the portable monitoring device may autonomously adjust the HVAC system to prevent the HVAC system from overheating the user's sleeping environment. In another example, the portable monitoring device may determine that a user's blinds are open and determine that a sleep goal of the user is to sleep in a darker environment (i.e., with the blinds closed). In this example, the portable monitoring device may autonomously close the blinds. In another example, the portable monitoring device may document (e.g., audio record, video record, photograph, etc.) a spouse, a partner, a pet, etc. disturbing a sleeping environment of a user. In this example, the portable monitoring device may document these types of disturbance and autonomously set one or more goals for the user to prevent these types of disturbances in the future. The portable monitoring device may include augmented reality capabilities for augmenting a user's sleep environment. In one example, the augmented reality capabilities may project a scene (e.g., a tropical island, a beach, etc) into the sleep environment of the user. In another example, the augmented reality capabilities may cause a speaker in the environment to produce a sound (e.g., waves, thunder, a fan, classical music, etc) which may help the user achieve a sleep goal.

The sleep collecting process 300 may include the participants completing sleep diaries 304. For example, participants may complete sleep diaries 304 online that record information about their sleep including duration, quality, time of day when sleep occurred, and other information that provide for generating sleep health assessments 306 of the participants sleep program progress. In some example, spouses/partners 308 may also provide sleep health observations and complete sleep diaries to provide additional observation data that may provide for generating sleep health assessments 306. Participants may also receive an environmental recording device 310. The environmental recording device may accurately record the environmental conditions of the participant's sleeping environment. The environmental recording device may include a bedside console that tracks environmental factors that have a direct correlation to quality of sleep. The environmental recording device may also include the ability to aggregate sensor data from medical devices to provide a very accurate assessment of sleep/wake history and the impact of the sleep intervention. The sleep data collecting process 300 may include obtaining previous counselor assessments 312 to help track participant progress. An updated participant file with the data collected from the current week of the program may then be forwarded to a coaching process for further evaluation 314.

In some instance, the sleep data collecting process 300 may include weighting the data from the various sources based on reliability. For instance, the process 300 may include relying more heavily on the data captured by the monitoring device and environmental recording device as compared to the sleep diaries and/or assessments since the devices may provide more accurate raw data that is not typically susceptible to human manipulation and/or memory.

Figure 4:
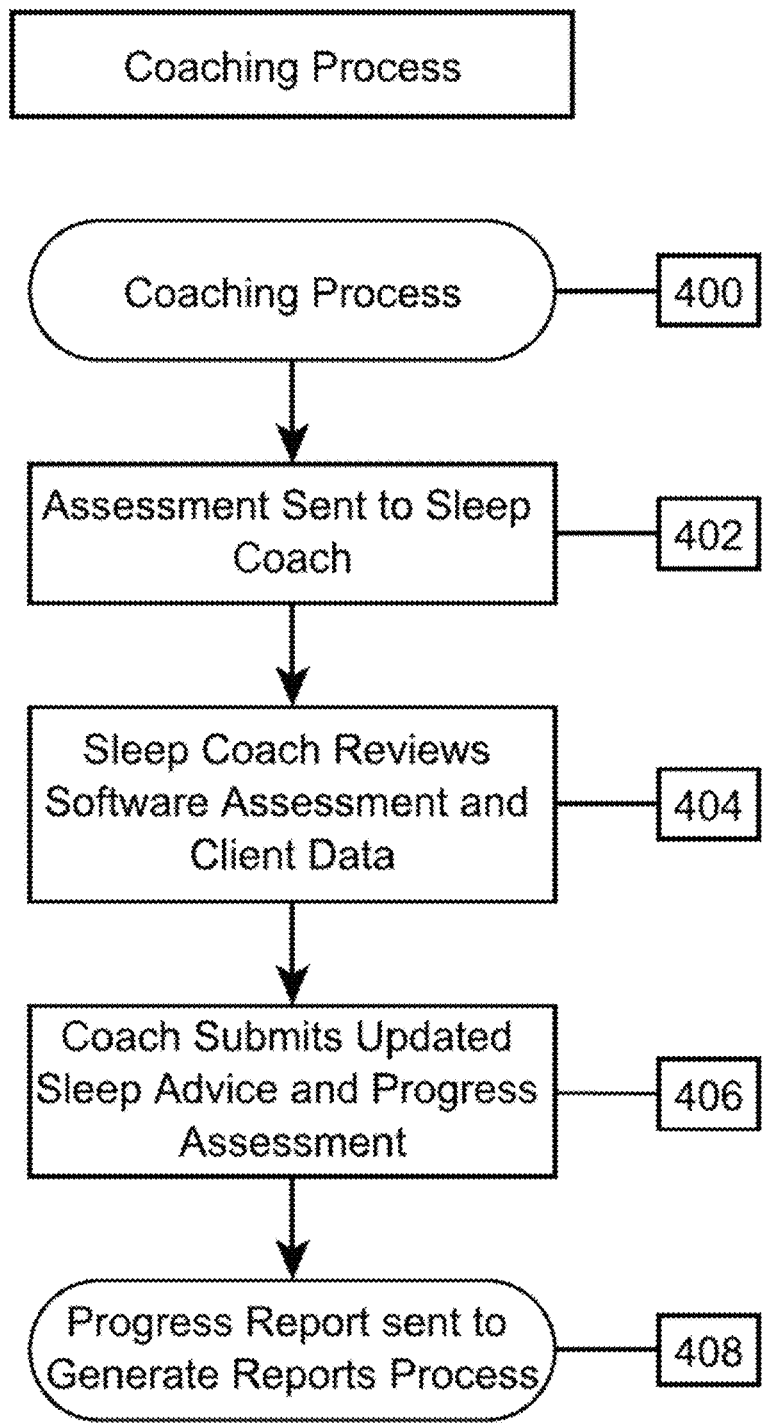
FIG. 4 illustrates a flow diagram of an example coaching process.

FIG. 4 illustrates a flow diagram of an example coaching process. During the coaching process, sleep counseling applications receive assessments 400 from the collecting data stage. The sleep counseling application may review the assessed participant data 404. The sleep counseling application may update sleep advice. The sleep counseling application may create a progress report 406. In some examples a machine learning algorithm may provide for selection of particular sleep goals. In another example, predictive analytics may determine a highest probability of success by grouping certain factors, various goals, and/or sleep improvement suggestions based on a user's age, sex, body mass index (BMI), neck size, biophysical markers, etc. In some examples, the sleep counseling system may determine certain groupings of factors that would be most effectively impacted by certain groupings of sleep improvement goals.

For example, an obese male in his 40s may have a different selection of goals compared to a thin, female in her 20s. The algorithm will be refined to provide the most effective goal suggestions based on the experiences of previous similar users. Moreover, each disease state like diabetes, cardiovascular disease, cancer, obesity, sleep apnea, may have different factors that impact outcomes compared to each other. The algorithm may be validated for each individual and then again for that individual with a certain disease state. For example, it is known that sleep is important factor when treating diabetes and regulating glucose and insulin levels. Lack of adequate sleep may often complicate diabetes management by increasing the amplitude of the blood glucose and insulin levels. Furthermore, there may differences in sleep needs across individuals necessitating creating a customized sleep treatment plan for each individual. Determining these individual sleep needs may be critical for effective treatment and may be found through measuring sleep wake history over time and comparing that to a user's blood glucose readings. In one example, over time, an user may learn their particular sleep needs if they see a spike in their glucose levels when they average under about six or five hours of sleep per night. Determining a user's own sleep needs can be effective helping to treat many difficult and costly disorders. The progress report may then be sent to the generate reports process 408.

Additionally there may be two validated measures for recording sleep. Electroencephalogram (EEG) and Actigraphy. EEG may be preferred but due to cost and the hassle involved in applying the various sensors it may only be used for short periods of time as in one or two days/nights. Actigraphy may also be preferred, and may be validated for use over long periods of time to determine cumulative sleep/wake history. Actigraphy may be based on movement and the amplitude of acceleration in a certain period of time to determine types of movement (e.g., walking, running, sleeping, etc.). Actigraphy may be limited in accurately ascertaining certain types of movement such as the difference between sitting and being restful but awake and napping. These activities may be very similar and difficult to discern with actigraphy alone. The sleep counseling application may use additional data points from the environment like light, sound, and biophysical sensor (e.g., electromyography (EMG)) to detect muscle movement and photoplethysmogram (PPG).

Figure 5:
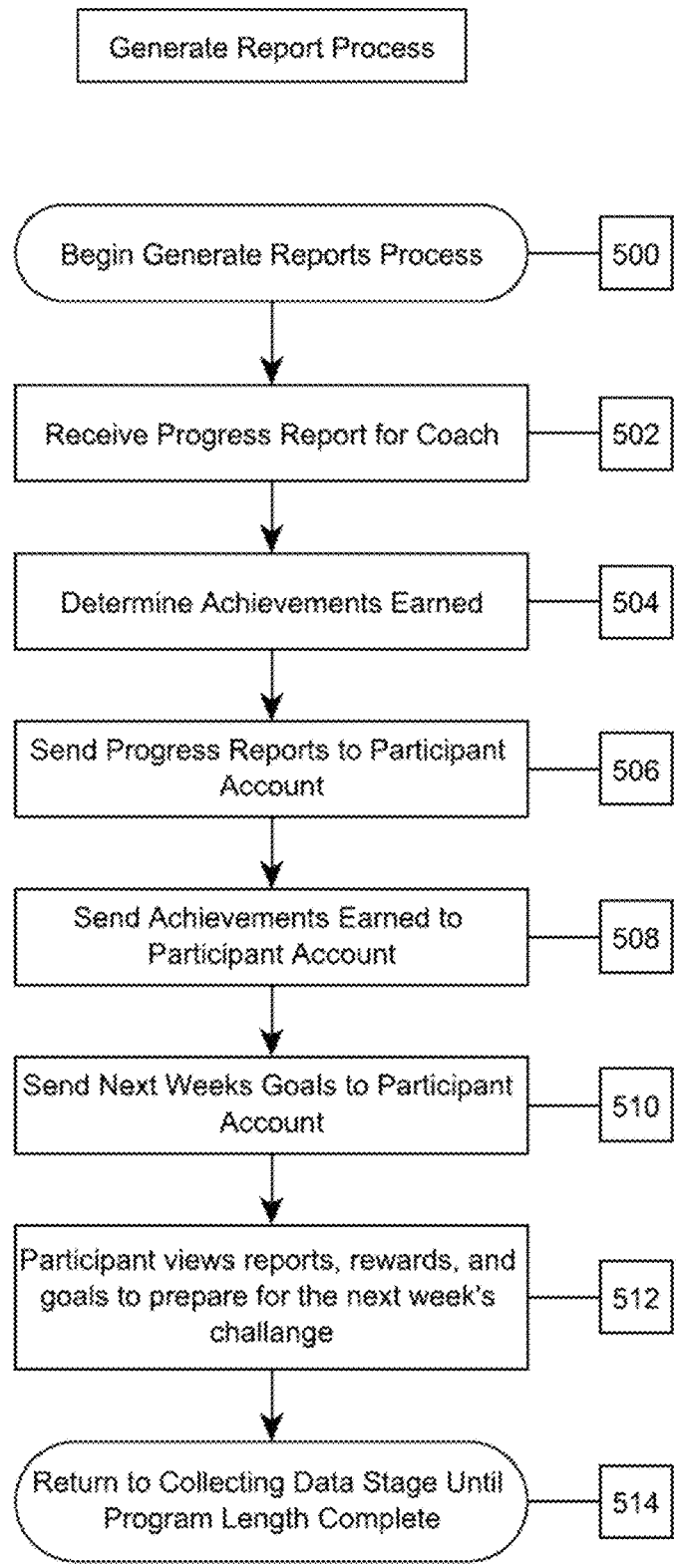
FIG. 5 illustrates a flow diagram of an example report generating process.

FIG. 5 illustrates a flow diagram of an example report generating process. At a beginning 500 of the generate reports process the sleep counseling application may receive raw progress reports 502. The sleep counseling application may use the raw progress report to determine achievements earned and weekly goals 504. Progress reports may then be sent to the participant 506. The achievements earned for the week may be sent to the participant account 508. The next week's goals may be sent to the participant's account 510. The participant may view the reports, rewards, and goals for the next week's challenge 512 and may have an option to discuss his or her progress with a sleep counselor before beginning the next week. Participants may then return to the collecting data stage to repeat the sleep program cycle until the custom program length is complete 516.

Figure 6:
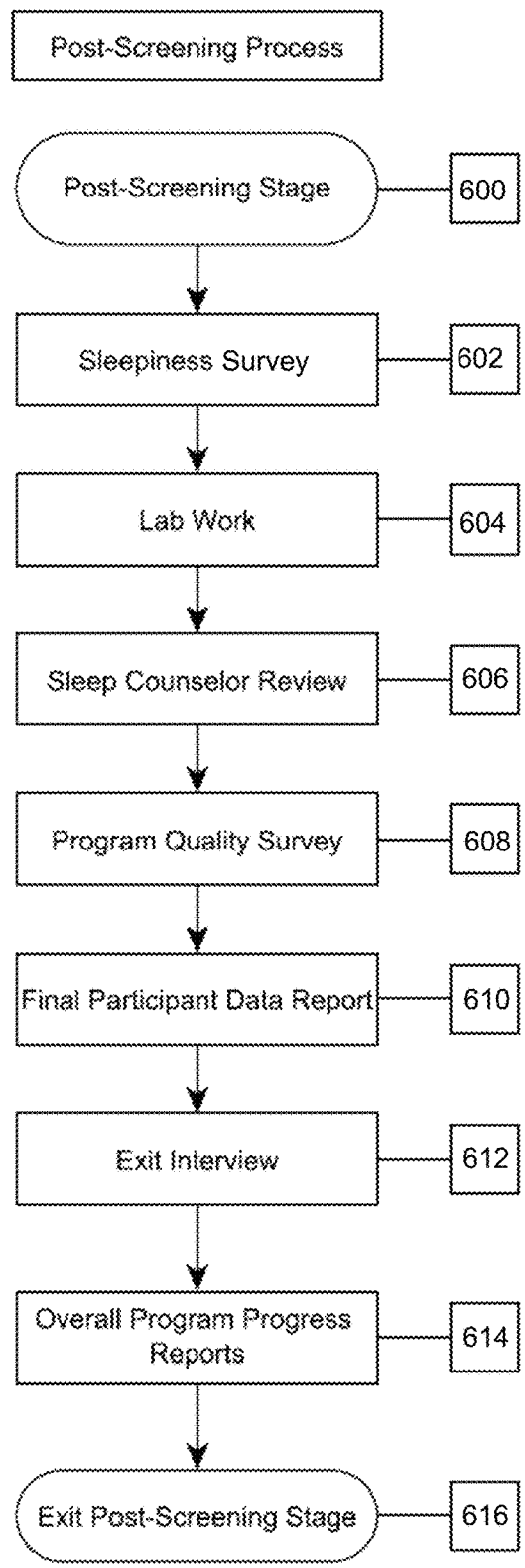
FIG. 6 illustrates a flow diagram of an example post-screening process.

FIG. 6 illustrates a flow diagram of an example post-screening process. FIG. 6 shows a flow chart of how a final report is generated. The sleep application may begin with a post-screening stage at operation 600. Operation 600 may be followed by operation 602. Operation 602 may represent analyzing the data collected during the sleep challenge program. The analyzing of the data collected during the sleep challenge program may include, the sleep application determining the achievements earned by the participant. Further, the analyzing of the data collected during the sleep challenge program may include, assessing the goals achieved by the participant. The post-screening process may continue at operation 604. Operation 604 may represent a comparison chart of pre-program and post-program of blood work labs results. For example, the sleep application may create a comparison chart of the pre-program blood work lab result with the post-program blood work lab results. Further, the sleep application may create a comparison chart of the pre-program physical with the post-program physical. The post-screening process may include operation 606. Operation 606 may represent a sleep counselor review and/or sleep application review of data representing the sleepiness survey and/or data representing the lab work. A comparison chart of the pre-program and post-program sleep quality based on the sleep diaries and the sleep surveys may be created at operation 608. The sleep application may generate a final participant data report at operation 610. A recommendation for further participation in the sleep challenge program may be created at operation 612. A report of the overall improvements made during the sleep challenge program and a tentative guideline for further improvement may be generated at operation 614. The final report may be sent to the post-screening process to be delivered to the participant at operation 616.

Figure 7:
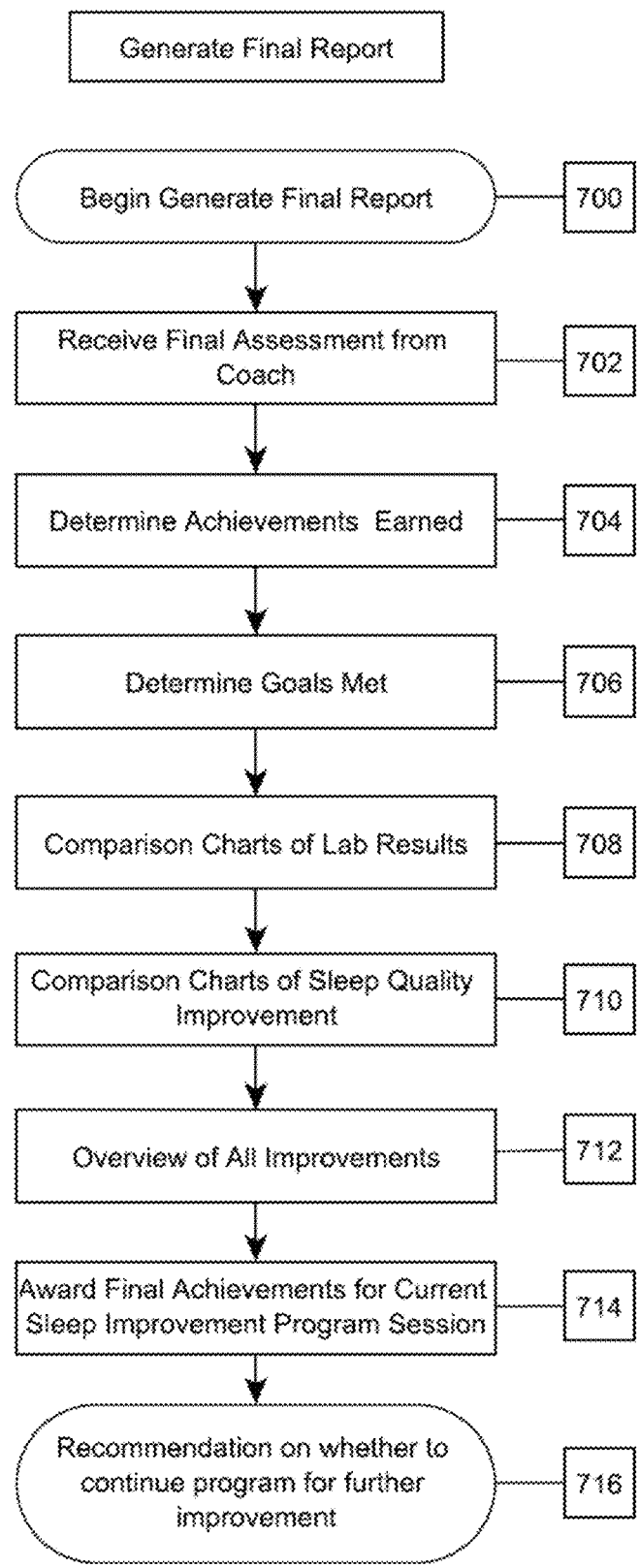
FIG. 7 illustrates a flow diagram of another example report generating process.

FIG. 7 illustrates a flow diagram of another example report generating process. FIG. 7 shows a flow diagram of the post-screening process. Participants may come to the end of their personally designed sleep challenge program and may participate in the post-screening process 700 to generate a set of comparison data to measure their improvement during their participation in the sleep challenge program. The sleep application may receive the final report 702 about the participant's progress during the sleep challenge program. The sleep application may use the final progress report to review 704 the participant progress during the sleep challenge program. Participants may retake the sleepiness survey 706. Participants may also receive new blood work to measure improvements 708. Participants may be given a program quality survey that measures their satisfaction with their experience in the program and helps improve the functionality of the program 710. Participants may participate in an exit interview where they discuss their progress with a sleep counselor 712. An overall program progress report 714 may be sent to the participant and based on the information received the participant may decide to repeat or end the program after they exit the post-screening stage 716.

Figure 8:
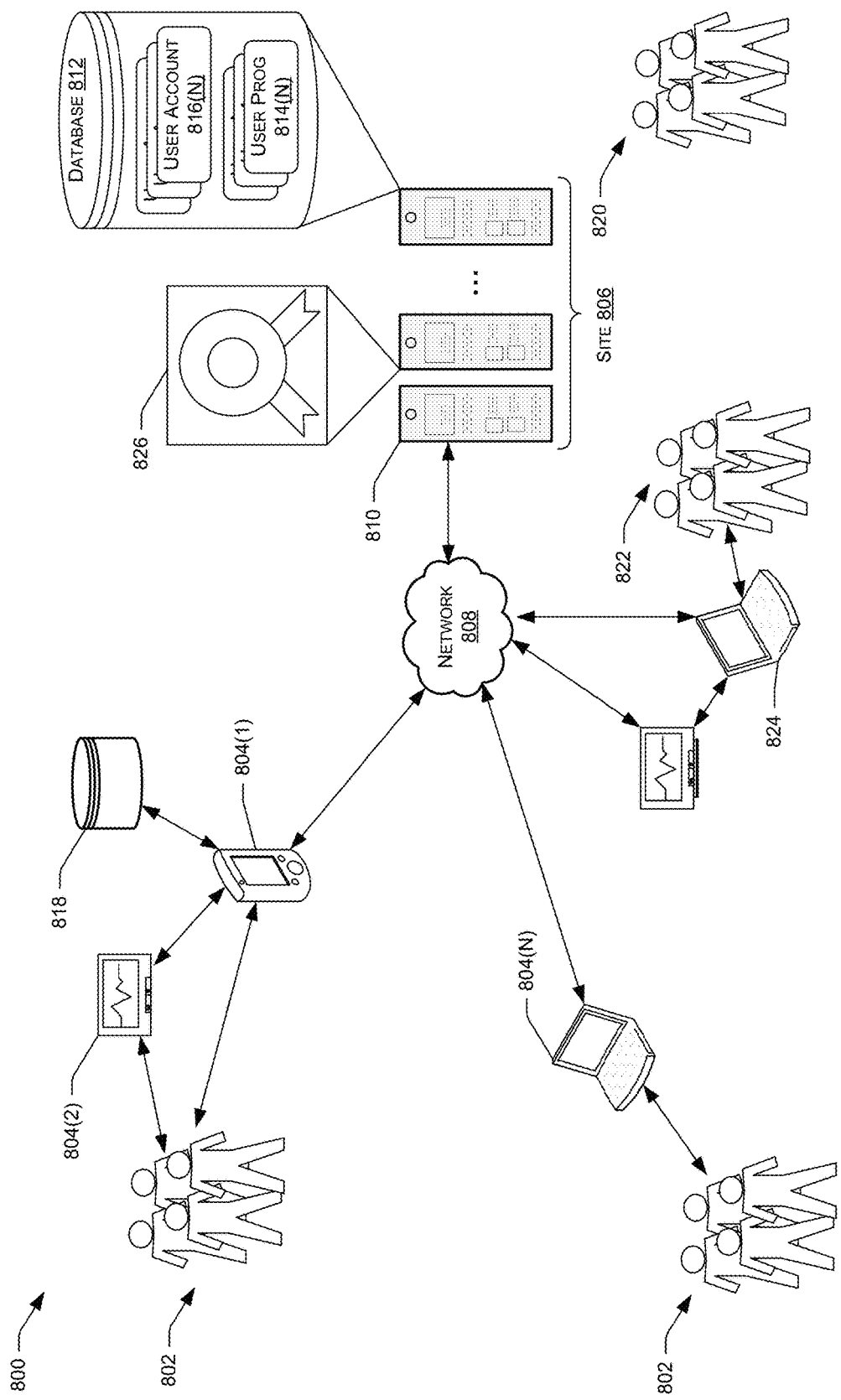
FIG. 8 illustrates an overview of an example system for providing sleep improvement for a user.

FIG. 8 illustrates an overview of an example system for providing sleep improvement for a user. FIG. 8 shows an example architecture 800 that may implement a platform for improving sleep habits of users 802. This platform may also provide personally designed sleep improvement programs that allow the users 802 to track valuable information regarding their sleep habits and that allow the users 802 to identify sleep characteristics.

As shown, architecture 800 includes computing devices 804(1), 804(2), . . . , 804(N) employed by the users 802, such as a mobile phone 804(1) (e.g., smartphone), a wearable device 804(2), a personal computer 804(N), etc. While FIG. 8 illustrates a mobile phone, a wearable device, and a personal computer, the users 802 may employ other computing devices, such as bedside consoles, wearable sleeves, portable media players, tablet computers, notebooks, and the like. Moreover, one or more of the computing devices 804(1)-804(N) may be communicatively coupled to a control unit (e.g., environmental control unit (ECU)) for operating electronic devices, including heating, ventilation, air conditioning (HVAC) systems, appliances (e.g., refrigerator, microwave, oven, etc.), security systems, cameras, electric blinds, etc. associated with a home of a user. For example, one or more of the computing devices 804(1)-804(N) may be communicatively coupled to a control unit (e.g., environmental control unit (ECU)) for operating electronic devices, including HVAC systems, appliances, security systems, cameras, electric blinds, etc. to autonomously control these electronic devices based at least in part on a user's sleep improvement program. For example, the user's sleep improvement program may include one or more goals of the user and the one or more computing devices 804(1)-804(N) may autonomously control electronic devices, including HVAC systems, appliances, security systems, cameras, speakers, electric blinds, etc. based at least in part on the one or more goals of the user.

Whatever the specific device, the users 802 employ computing devices 804(1)-804(N) to communicate with a site 806 via a network 808. The site 806 may include one or more servers 810 (e.g., web application server) that may provide personalized Graphical User Interfaces (GUIs), associated with the sleep improvement programs, to the users based on their individual sleep characteristics. The network 808 represents any one or combination of multiple different types of networks, such as the Internet, cable networks, wireless networks, and wired networks. In this example, the site 806 stores or has access to a database 812 that includes, amongst other things, a multitude of user sleep improvement programs 814(1), . . . , 814(N) that each correspond to one of the users 802. Each of the users may authenticate at the site 806 and, after this authentication, are allowed to contribute content to a corresponding account 816(1), . . . , 816(N) of the user and/or receive content from a corresponding account of the user.

The servers 810 may have storage and processing capabilities that hosts the site 806. The servers 810 may be embodied in any number of ways, including as a single server, a cluster of servers, a server farm or data center, and so forth, although other server architectures (e.g., mainframe) may also be used. Whatever its architecture, the site 806 serves personalized sleep improvement programs to the computing devices 804(1)-804(N) of users 802.

In some instances, each user sleep improvement programs 814(1)-814(N) includes information about a corresponding user. This information includes, for instance, data identifying sleep characteristics of the user, data identifying factors impacting a sleep of the user, data identifying goals associated with the user, data identifying responses to queries by the user, data identifying actions taken by the user, data identifying a sleep-related performance of the user, data identifying rewards for the user, or any other information regarding the user. Further, the information may include data representing an answer by the user to a question in a survey, data representing a psychographic profile of the user, data representing a medical record of the user, the medical record including a record of a physical or a record of a lab value, data representing data collected by a wearable device, and/or data representing data collected by an environmental recording device. Moreover, the information may include an initial depression/sleepiness screening survey. This survey may be a combination of validated questionnaires called "Sleepiness Scales."

Sleepiness Scales may be "The Epworth Sleepiness Scale," "The national Sleep Foundation Sleepiness Test," "The Stanford Sleepiness Scale," or "The Karolinska Sleepiness Scale." A survey, based at least in part on the above listed, pre-validated sleepiness scales, may provide a "score" of the individual user. Based on this score, users may be advised to opt-in to the sleep improvement programs, or seek further analysis of exclusionary criteria with a Primary Care Physician. The information may include a psychographic profile of individual users. The information may include standard medical records, patient reports, previously recorded sleep data, vital signs, and laboratory values. The information may include data collected by a wearable device such as activity levels, user heart rate, environmental noise, environmental temperature, user body temperature, user cortisol levels.

Moreover, the information may include data identifying actionable items. Actionable items may be relevant performance skills associated with preferred sleep habits over a normally distributed population. For example, the actionable items may be data associated with distractions during sleep preparation tasks, data associated with completed sleep preparation tasks, data associated with acquired items needed for healthy sleep environment, data associated with seeking help/clarification to support sleep hygiene needs, data associated with gaining support of others in household to support sleep hygiene needs, data associated with moving through sleep preparation tasks in an effective sequence, data associated with initiating sleep participation tasks, data associated with gathering necessary sleep hygiene materials, data associated with adjusting sleep hygiene tasks, or data associated improving sleep hygiene routine with experience.

In some instances, the site 106 provides or aggregates this information for presenting on the personalized sleep improvement programs. In some examples, the site 106 provides or aggregates this information for communicating to the one or more computing devices 804(1)-804(N) and/or a control unit (e.g., environmental control unit (ECU)) for operating electronic devices, including heating, ventilation, air conditioning (HVAC) systems, appliances (e.g., refrigerator, microwave, oven, etc.), security systems, cameras, electric blinds, etc. associated with a home of a user.

In some examples, one or more of the users 802 may wear computing device 804(2). The computing device 804(2) may collect data associated with information such as activity levels (defined as physical movement such as steps taken or the lack of movement indicating periods of rest), user pulse/heart rate, environmental noise, environmental temperature, user body temperature, user cortisol levels. The computing device 804(2) may use accelerometers for measuring movement, gyroscope to measure changes in angle, electrodes to measure changes in current flow over the skin (galvanic skin response), sensors to measure temperature outside and from the skin, a microphone to measure noise filtered to certain frequencies such as snoring, sensors to measure light intensity, frequency and wavelength. In some examples, the computing devices 804(2) may communicate the collected data to the device 804(1) for further processing. In other examples, the computing device 804(2) may communicate the collected data to the site 806. The computing device 804(1) may store or have access to a database 818. In some examples, one or more of the users 802 may not wear computing device 804(2). The users 802 not wearing computing devices 804(2) may optionally input data associated with information such as activity levels into an optional user interface displayed by a computing device (e.g., a computing device 804(N)).

In some examples, one or more of the users 802 may use a computing device such as a bedside console for example. The bedside console may include sensors capable of recording data associated with light exposure, sound, temperature and humidity. The bedside console may be valuable in creating a more accurate measure and algorithm of cumulative sleep/wake history by using these additional data points to confirm or refute periods of low activity where traditionally actigraphy may be less accurate. As discussed above, the bedside console may be communicatively coupled to a control unit (e.g., environmental control unit (ECU)) for operating electronic devices, including heating, ventilation, air conditioning (HVAC) systems, appliances (e.g., refrigerator, microwave, oven, etc.), security systems, cameras, electric blinds, etc.

In some examples, one or more of the users 802 may use a computing device such as a wearable sleeve that may track personal sleeping patterns along with factors that affect quality, and duration of sleep. For example, a wearable sleeve may measure heart rate and movement of the user. The wearable sleeve may be communicatively coupleable with the bedside console.

FIG. 8 illustrates one or more professionals 820 may back the site 806. For example, after data has been collected from a user, a professional 820 may examine the data to determine if the user requires a referral to a sleep professional for further evaluation for a possible sleep disorder. In some examples, one or more sleep counselors 822 may make sleep health assessments of the user's sleep program progress. Spouses/partners may also provide sleep health observations and complete sleep diaries to provide observation data that the sleep counselors may user to make assessments. Sleep counselors 822 may be a coach, a business manager, an assistant, etc. The sleep counselors 822 may download user data from the site 806, perform analysis, and upload user data to the site 806. The sleep counselors 822 may download user data, perform analysis, and upload user data to the site via a computing device 824.

FIG. 8 illustrates the site 806 may include an incentive/rewards system 826. For example, the site 806 may include the incentive/rewards system 826 that may provide feedback and rewards to users 802. The incentive/rewards system 826 may gamify the sleep improvement programs by providing users 802 with feedback through rewards and/or other game elements. The incentive/rewards system 826 may use game elements in order to inform participants about their performance and progress associated with the sleep improvement programs. The game elements may include points, badges, progress bars, coupons, etc. The progress and performance may be determined by actionable items. The users 802 may use the feedback to adjust their actions in order to get closer to their goals. The incentive/rewards system 826 may include an educator system. The educator system may include an educator algorithm that may provide recommendations for websites (e.g., blogs) or videos about sleep specific research and sleep related research based on psychographic and activity data. The recommendations may be built up by repeated interactions between the users 802 and the site 806. The incentive/rewards system 826 may include a quiz system that may create quizzes based at least in part on the users 802 interactions with the educator system. The quiz system may use spaced retrieval and/or retrieval practice education techniques to help participants learn better sleep habits.

FIG. 9 illustrates an example Graphical User Interface (GUI) 900 for requesting data identifying sleep characteristics of a user. FIG. 9 illustrates the example GUI 900 may present a survey 902 requesting data identifying sleep characteristics of a user. For example, the survey 902 may present questions 904 regarding an exterior environment 906 to the user to generate goals based on selected factors which will match the user's lifestyle. Further, while FIG. 9 shows the survey 902 presenting questions regarding an exterior environment, the survey 902 may present questions regarding an interior environment, artificial light, natural light, sleep behavior, lifestyle behavior, job behavior, consumption behavior, other behavior, etc. to the user to generate goals based on selected factors which will match the user's lifestyle. In some examples, the survey (e.g., sleep survey) may be presented to the user when the user first opens a sleep improvement program and prompt the user for data identifying existing sleep habits of the user. As discussed above, this survey may be a combination of validated questionnaires called "Sleepiness Scales." Sleepiness Scales may be "The Epworth Sleepiness Scale," "The national Sleep Foundation Sleepiness Test," "The Stanford Sleepiness Scale," or "The Karolinska Sleepiness Scale." A survey, based at least in part on the above listed, pre-validated sleepiness scales, may provide a "score" of the individual user. Moreover, exclusionary criteria may not prevent a user from enrolling into the system. For example, exclusionary criteria are an indicator of further needed medical attention that may not be provided by the system. The exclusionary criteria may include possible sleep disorders such as obstructive sleep apnea, urological conditions (benign prostatic hyperplasia (BPH), overactive bladder), hyper-thyroidism, hypo-thyroidism, type I diabetes, type II diabetes, moderate to severe depression, cancer, neurological conditions, night sweats (menopausal), children that reside in the house that require attention during sleeping hours.

Figure 10:
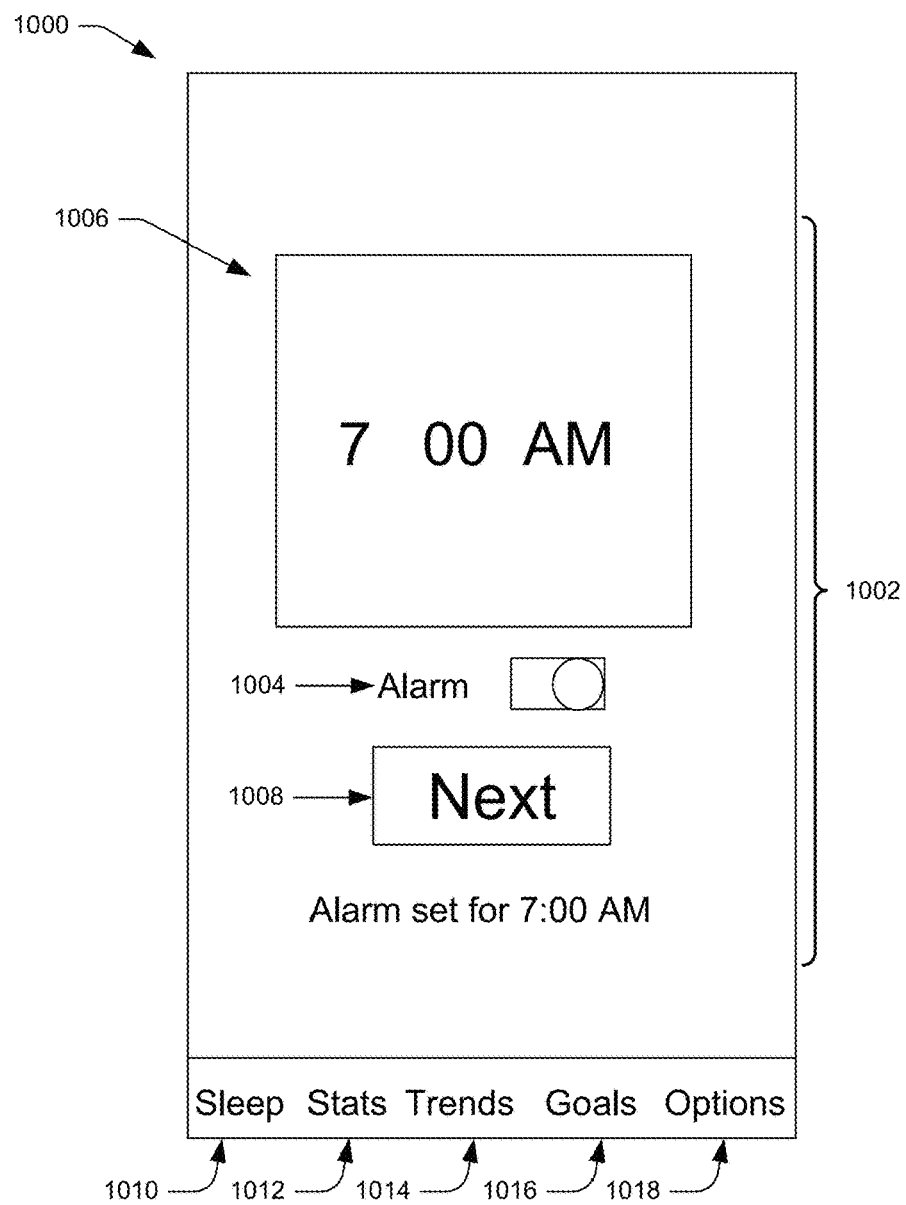
FIG. 10 illustrates a Graphical User Interface (GUI) for presenting an alarm.

FIG. 10 illustrates an example Graphical User Interface (GUI) 1000 for presenting an alarm 1002. Alarm 1002 allows the user to wake up at a preselected time. The alarm 1002 may include an on/off toggle 1004 to provide for turning the alarm 1002 on and/or off. A display 1006 displaying a selected time. The alarm 1002 may include a user selectable icon 1008, that when selected, schedules the alarm. FIG. 10 illustrates different modes of the sleep improvement program. For example, FIG. 10 illustrates a sleep mode 1010, a statistics mode 1012, a trends mode 1014, a goals mode 1016, and an options mode 1018.

Figure 11:
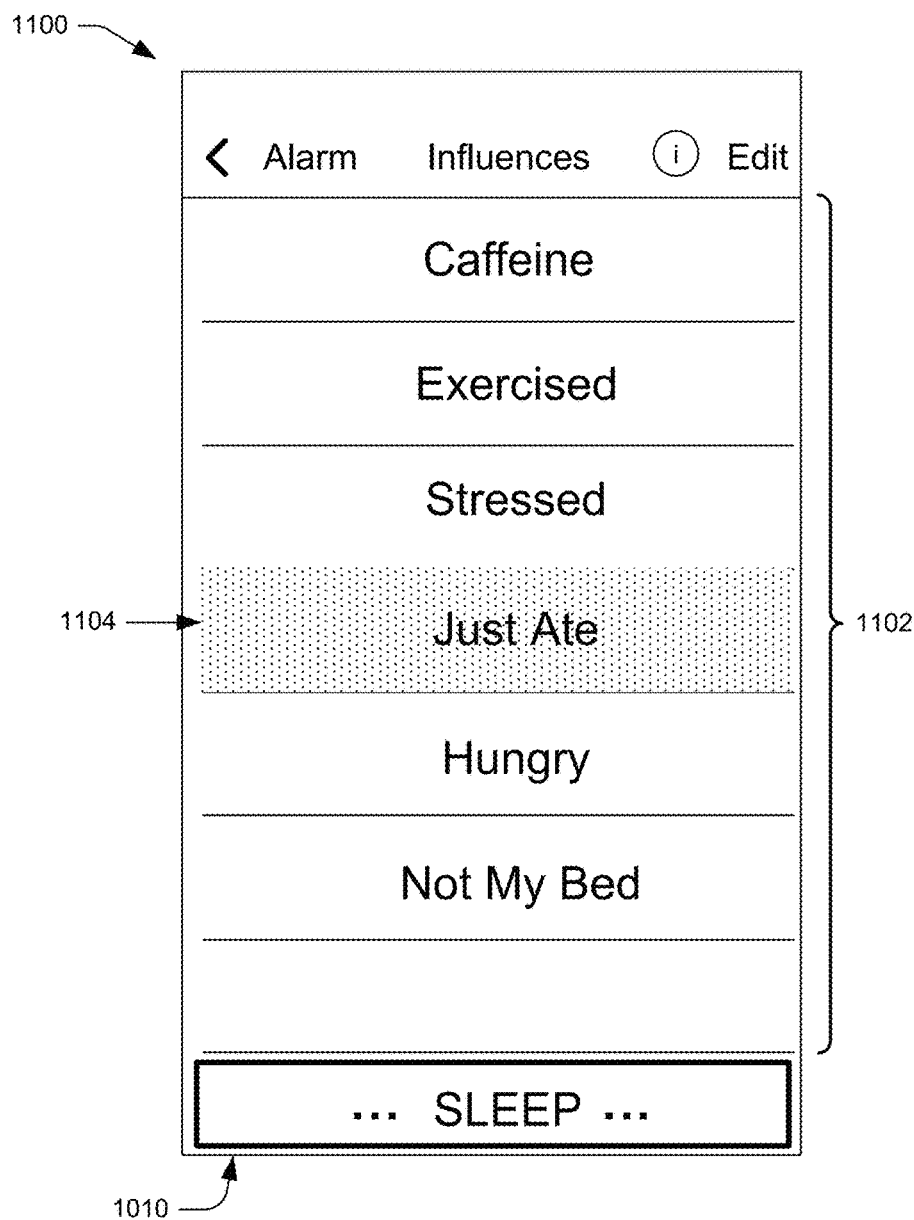
FIG. 11 illustrates a Graphical User Interface (GUI) for requesting data identifying influences impacting a daily routine of a user.

FIG. 11 illustrates an example Graphical User Interface (GUI) 1100 for requesting data identifying influences impacting a daily routine of a user. The example GUI 1100 may represent the sleep improvement program in the sleep mode 1010. The example GUI 1100 may allow a user to select one or more influences 1102 that may have impacted the user's daily routine. For example, FIG. 11 shows the user has selected (represented by stippled portion) "Just Ate" influence 1104 as an influence impacting the daily routine of the user. The user may add or delete influences to the GUI 1100 to better calibrate the sleep improvement program towards the user's individual needs. During the sleep mode 1010, motion data may be collected which can be viewed later in other views (described in detail with regard to FIG. 12 below).

Figure 12:
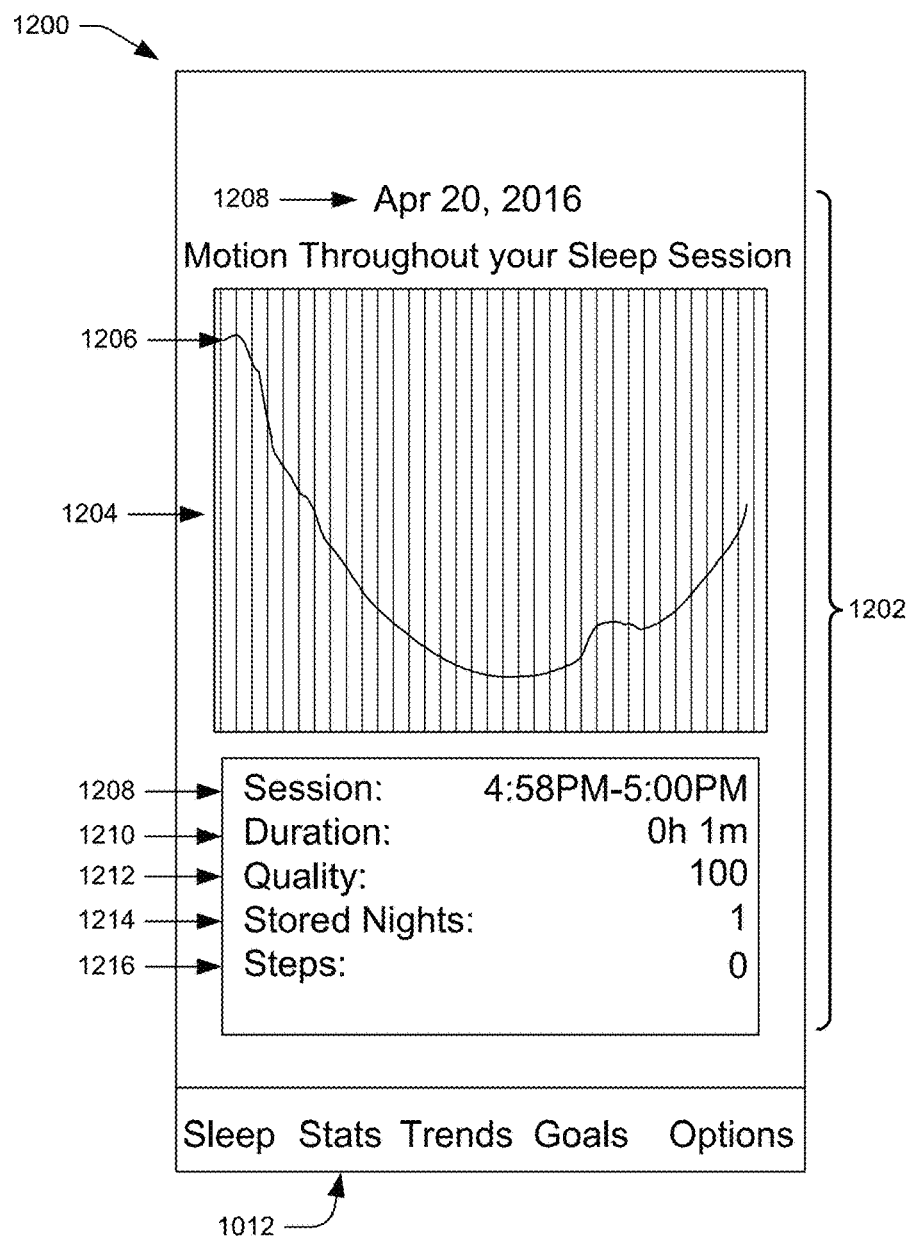
FIG. 12 illustrates a Graphical User Interface (GUI) for presenting statistics of sleep of a user.
Figure 13:
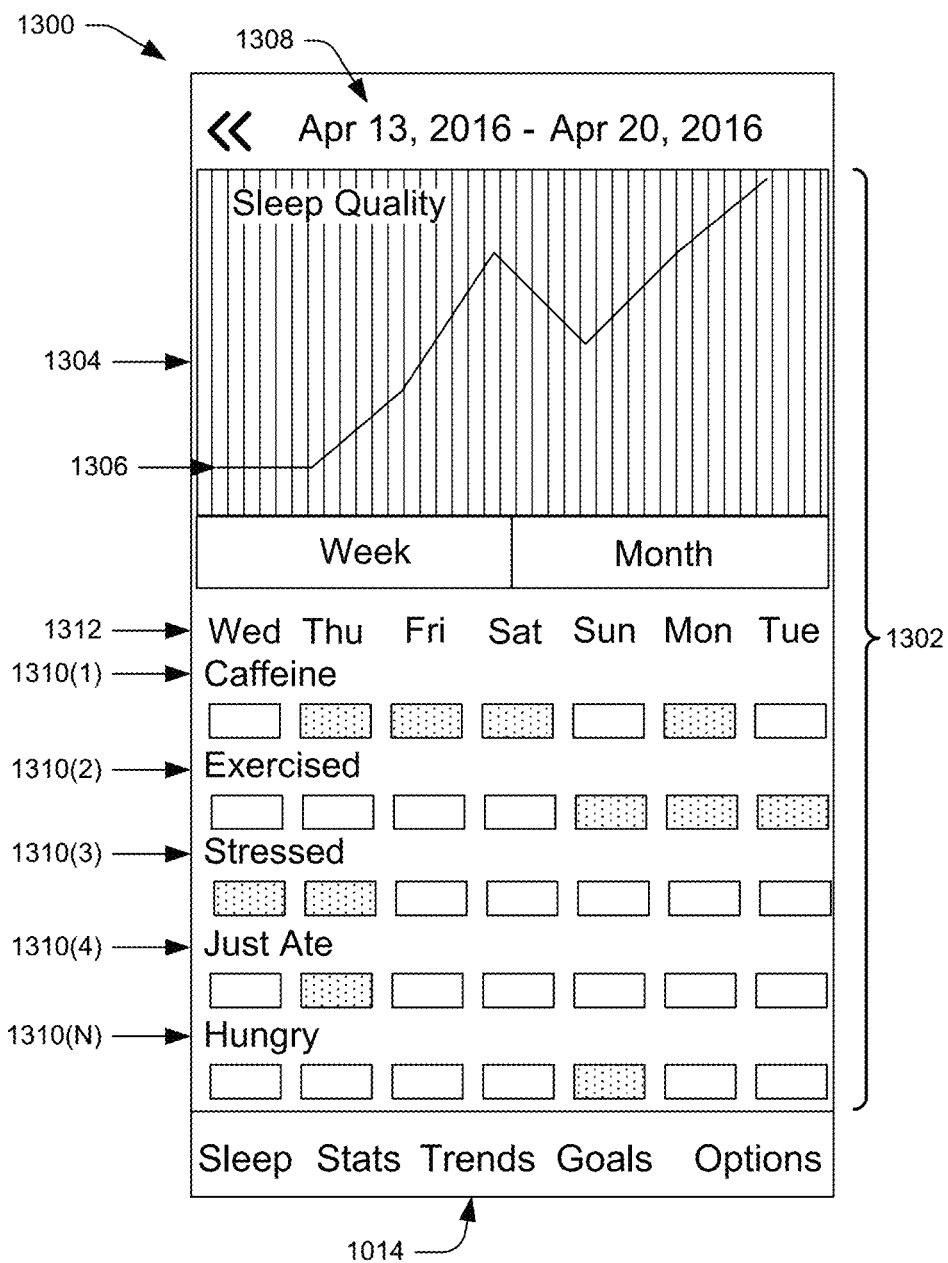
FIG. 13 illustrates a Graphical User Interface (GUI) for presenting trends of sleep of a user.

FIG. 12 illustrates an example Graphical User Interface (GUI) 1200 for presenting statistics 1202 of sleep of a user. The example GUI 1200 may represent the sleep improvement program in the statistics mode 1012. The GUI 1200 may include a display 1204 that may present a graph 1206 of a set of sleep data for a selected date 1208. The GUI 1200 may allow a user to view start and end time statistics 1210, duration statistics 1212, sleep quality statistics 1214, total stored nights statistics 1216, steps taken since last session statistics 1218 for the selected sleep session FIG. 13 illustrates an example Graphical User Interface (GUI) 1300 for presenting trends 1302 of sleep of a user. The example GUI 1300 may represent the sleep improvement program in the trends mode 1012. The GUI 1300 may include a display 1304 that may present a graph 1306 of a sleep quality for a selected duration 1308 (e.g., a course of a week, month, quarter, etc.). In some examples, the GUI 1300 may allow a user to view how well a user has slept over a course of a week or a month. The GUI 1300 may include one or more influences 1310(1), 1310(2), 1310(3), 1310(4), . . . , 1310(N) that may have affected the user's sleep for each day 1312. For example, FIG. 13 shows caffeine 1310(1) effected a user on Thu, Fri, Sat, and Mon (represented by stippled boxes). Thus, the GUI 1300 may provide for a user to see his or her sleep quality in the graph 1306 and see his or her sleep influences 1310(1)-1310(N) listed for each day Mon-Fri.

Figure 14:
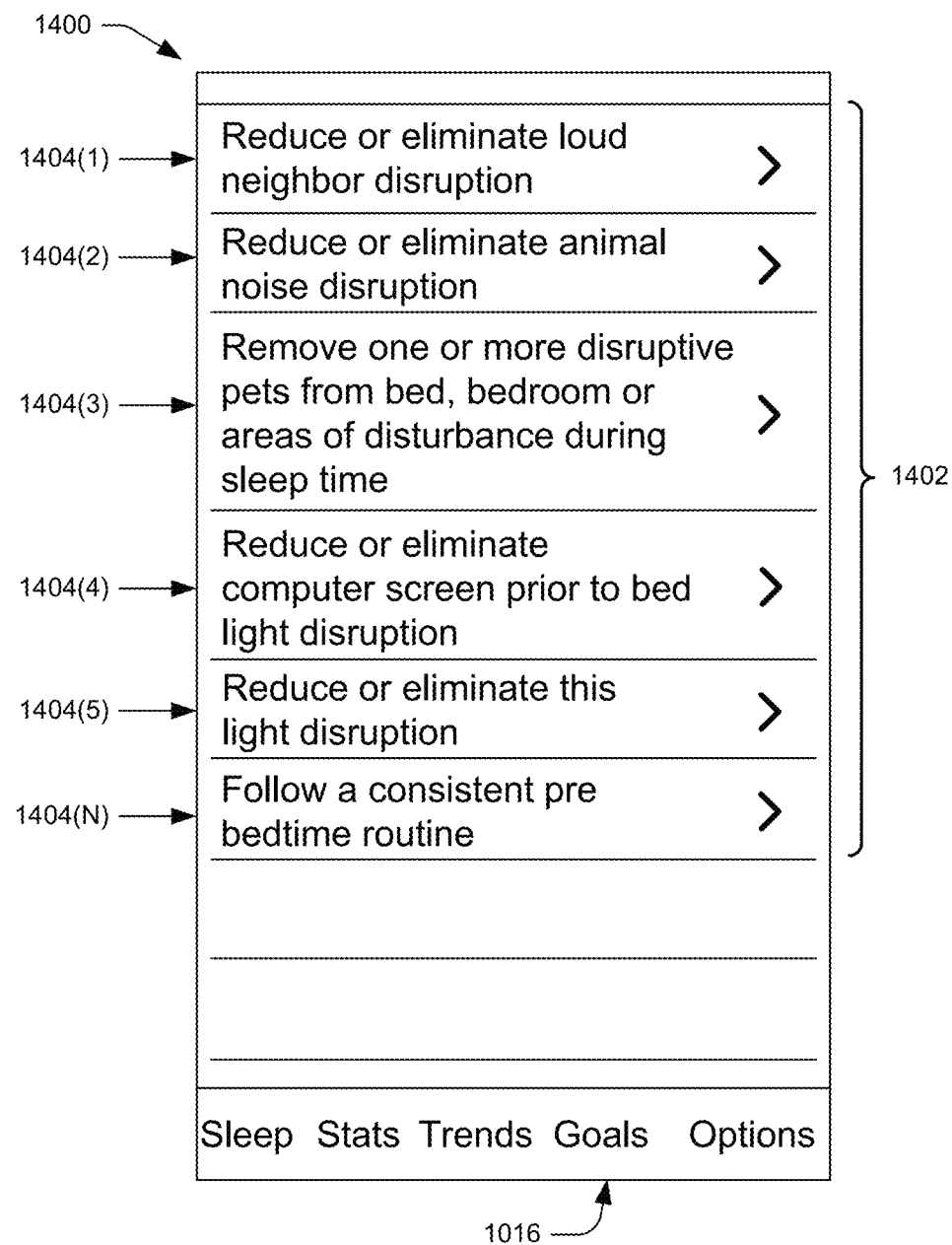
FIG. 14 illustrates a Graphical User Interface (GUI) for presenting goals of a user.

FIG. 14 illustrates an example Graphical User Interface (GUI) 1400 for presenting goals 1402 of a user. The example GUI 1400 may represent the sleep improvement program in the goals mode 1016. The GUI 1400 may present one or more goals 1404(1), 1404(2), 1404(3), 1404(4), 1404(5) . . . , 1404(N) that a user should be working on based on how the user answered the survey 902 presented in the GUI 900. Selecting a goal of the one or more goals 1404 (1)-1404(N) may request a suggestion GUI (not shown) to be presented to the user. For example, clicking on a goal may give you suggestions on how to change your lifestyle to accomplish the goal.

CONCLUSION

Although the invention has been described in language specific to structural features and/or methodological acts, it is to be understood that the invention is not necessarily limited to the specific features or acts described. Rather, the specific features and acts are disclosed as illustrative forms of implementing the invention. For example, while embodiments are described having certain configurations, these configurations are merely illustrative.

What is claimed is:

1. A computerized method for providing sleep improvement for a user comprising:
    providing, to a device associated with the user, a first Graphical User Interface (GUI) requesting data identifying sleep characteristics of the user;
    receiving the data identifying the sleep characteristics of the user;
    assessing the data identifying the sleep characteristics; and
    providing, to the device associated with the user, a second GUI including at least one goal for the user based at least in part on the data identifying the sleep characteristics of the user.

2. The computerized method of claim 1, further comprising identifying at least one factor impacting a sleep of the user based at least in part on the assessing.

3. The computerized method of claim 1, further comprising providing, to the device associated with the user, a third GUI requesting data associated with at least one response by the user to at least one query;
    receiving the data associated with the at least one response by the user to the at least one query; and
    determining a sleep-related performance of the user based at least in part on the data associated with the at least one response by the user to the at least one query.

4. The computerized method of claim 1, further comprising providing, to the device associated with the user, a third GUI requesting data associated with at least one action taken by the user;
    receiving the data associated with the at least one action taken by the user; and
    determining a sleep-related performance of the user based at least in part on the data associated with the at least one action taken by the user.

5. The computerized method of claim 1, further comprising providing, to the device associated with the user, a reward to the user.

6. The computerized method of claim 1, wherein the first GUI requesting data identifying sleep characteristics of the user includes requesting data comprising an answer by the user to a question presented in a survey provided to the device associated with the user.

7. The computerized method of claim 1, further comprising providing, to the device associated with the user, a third GUI presenting a recommendation identifying at least one action operable by the user to accomplish the at least one goal.

8. The computerized method of claim 1, further comprising receiving data indicative of a request, from the device associated with the user, for a trend of sleep of the user; and
    providing, to the device associated with the user, a third GUI including the trend of sleep of the user.

9. The computerized method of claim 8, wherein the trend of sleep of the user includes a week trend of sleep of the user or a month trend of sleep of the user.

10. The computerized method of claim 1, further comprising receiving data indicative of a request, from the device associated with the user, for statistics of sleep of the user; and
    providing, to the device associated with the user, a third GUI including the statistics of sleep of the user.

* * * * *